United States Patent [19]

Gambale

[11] Patent Number: 5,063,935
[45] Date of Patent: Nov. 12, 1991

[54] CATHETER GUIDEWIRE WITH VARYING RADIOPACITY

[75] Inventor: Richard A. Gambale, Tyngsboro, Mass.

[73] Assignee: C. R. Bard, Inc., Murray Hill, N.J.

[21] Appl. No.: 644,487

[22] Filed: Jan. 18, 1991

Related U.S. Application Data

[63] Continuation of Ser. No. 344,017, Apr. 27, 1989, abandoned.

[51] Int. Cl.$^5$ .............................................. A61B 6/00
[52] U.S. Cl. .................................. 128/657; 128/772; 604/170
[58] Field of Search ........................... 128/656–658, 128/772; 604/95, 164, 170, 282

[56] References Cited

U.S. PATENT DOCUMENTS

| 3,749,086 | 7/1973 | Kline et al. | 128/772 |
| 4,215,703 | 8/1980 | Willson | 604/95 |
| 4,538,622 | 9/1985 | Samson et al. | 128/772 |
| 4,545,390 | 10/1985 | Leary | 128/772 |
| 4,577,637 | 3/1986 | Mueller, Jr. | 128/658 |
| 4,619,274 | 10/1986 | Morrison | 128/772 |
| 4,719,924 | 1/1988 | Crittenden et al. | 128/772 |
| 4,748,986 | 6/1988 | Morrison et al. | 128/772 |
| 4,763,647 | 8/1988 | Gambale | 128/772 |

OTHER PUBLICATIONS

Webster's II Dictionary, 1984, pp. 969, 970.

Primary Examiner—John D. Yasko
Assistant Examiner—Anthony Gutowski
Attorney, Agent, or Firm—Wolf, Greenfield & Sacks

[57] ABSTRACT

A guidewire for use with a catheter has varying radiopacity at its distal end. The guidewire includes a shaft having an outer helical coil attached to the distal region of the shaft, the coil extending distally beyond the distal end of the shaft and terminating in a tip weld. The outer coil is formed from a small diameter highly radiopaque wire. A smaller diameter inner helical coil, formed from a larger diameter highly radiopaque wire is disposed within the outer coil and is attached at its proximal end to the distal end of the shaft and at its distal end to the tip weld. The guidewire thus defines an arrangement which when viewed fluoroscopically will have a highly radiopaque distal portion and a moderately radiopaque proximal portion.

16 Claims, 1 Drawing Sheet

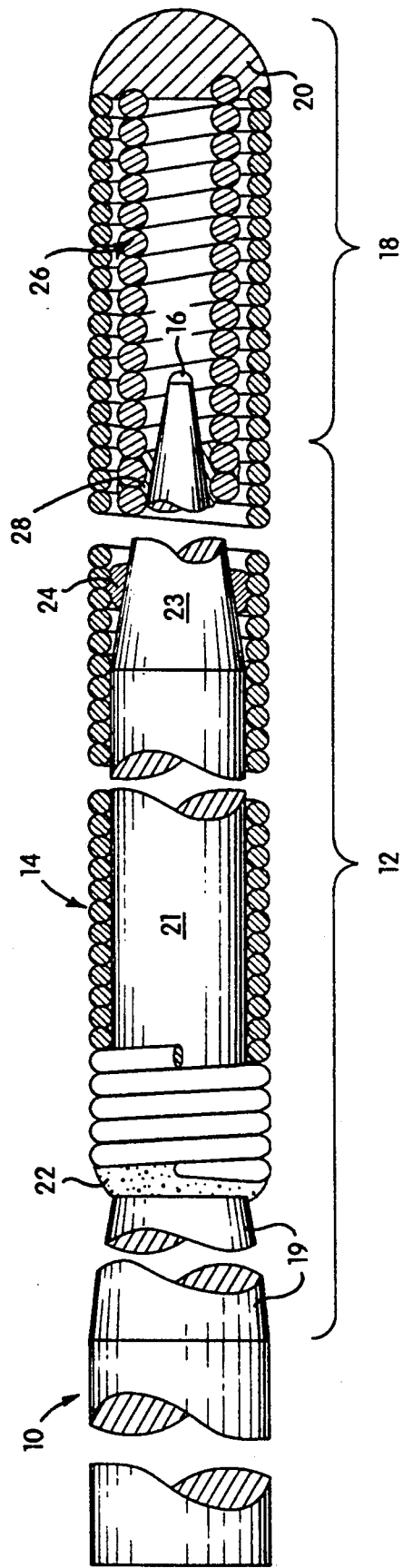

CATHETER GUIDEWIRE WITH VARYING RADIOPACITY

This application is a continuation of application Ser. No. 344,017, filed Apr. 27, 1989, now abandoned.

FIELD OF THE INVENTION

The invention relates to guidewires used to support and guide catheters as they are advanced through body lumens such as blood vessels.

BACKGROUND OF THE INVENTION

A wide variety of guidewires are used for various medical purposes in the treatment of the human body. Among the more common uses is in blood vessels to guide a catheter to a site within the patient's blood vessel to perform the procedure for which the catheter is adapted. For example, guidewires, particularly small diameter steerable guidewires perform an important function in percutaneous transluminal coronary angioplasty. Illustrative of such guidewires are those described in U.S. Pat. No. 4,545,390 (Leary) and U.S. Pat. No. 4,538,622 (Samson). Each of the guidewires described in those patents has a torsionally rigid, longitudinally flexible shaft and a flexible distal end that includes a coil, all or part of which is radiopaque so that the physician can monitor fluoroscopically the position and advancement of the guidewire in the patient's blood vessel. In procedures, such as coronary angioplasty, in which a catheter is advanced through the patient's arteries, it often is the practice to inject a radiopaque contrast liquid into the artery so that the shape and path of the artery may be visualized fluoroscopically. The radiopacity of the guidewire coil may be so dense as to visually obstruct part of the artery which the physician may desire to view when the contrast liquid is injected. For use in such instances, it would be desirable for the guidewire to be only partially radiopaque, that is, to form a light but visible grey shadow in some portions and a heavy, dark fluoroscopic image on another.

It also is desirable in the design of guidewires to coat the coil with a low friction material so as to reduce friction between the guidewire and catheter.

It is among the general object of the invention to provide guidewires having the foregoing desirable characteristics.

SUMMARY OF THE INVENTION

A guidewire, in accordance with the invention, has an elongate flexible shaft having a tapered distal portion. A helical coil formed from a radiopaque metal is mounted on the distal end of the shaft over the tapered portion, the tapered portion being received in and extending through the coil. The helical coil extends beyond the distal tip of the shaft. An inner coil is contained within the outer coil and is attached at its proximal end to the distal end of the shaft. The distal ends of both coils are attached to a distal tip weld. Both coils are formed from a highly radiopaque material. The outer coil, however, is formed from smaller diameter wire than that from which the inner coil is formed. Thus, the distal region of the coils which contains both coils will define a substantially more radiopaque region than the more proximal portion composed of the single outer coil formed from small diameter wire. The proximal portion forms a moderately radiopaque image which will not completely obstruct visualization of arteries into which radiopaque contrast liquid has been injected.

It is among the objects of the invention to provide a guidewire having a coil assembly at its distal end in which the coil assembly includes a highly radiopaque distal segment and a moderately radiopaque proximal segment.

DESCRIPTION OF THE DRAWING

The foregoing and other objects and advantages of the invention will be appreciated more fully from the following further description thereof, with reference to the accompanying drawing which shows a longitudinal sectional, fragmented illustration of the invention.

DESCRIPTION OF THE ILLUSTRATIVE EMBODIMENT

As illustrated in the drawing, the guidewire includes an elongated rotationally rigid, longitudinally flexible shaft 10 having a tapered region 12 at its distal end. An outer helical coil 14 is mounted to the distal end of the shaft 10, the tapered region 12 of the shaft 10 extending into and being received within the outer coil 14. The distal tip 16 of the shaft terminates short of the distal end of the coil assembly to define a flexible tip portion 18. The distal end of the outer coil 14 is attached to a rounded smooth tip weld 20. The proximal end of the outer coil 14 is attached to the shaft 10 at a proximal braze joint 22. The outer coil 14 also is attached to the shaft 10 adjacent the distal tip 16 at a distal brazed joint 24. The outer coil 14 is formed from relatively small diameter wire, of the order of 0.0010" to 0.0015" diameter.

The overall length of the guidewire may be of the order of 175 cm with the tapered region 12 of the shaft extending over a length of about 30 cm. The flexible tip portion 18 may extend over a length of about 2 cm. The shaft 10 includes an elongate proximal segment having a diameter of between about 0.012" to about 0.016". The proximal segment merges into a tapered segment 19 that extends over about 3 cm and tapers to a barrel segment 21 having a diameter of the order of 0.010" to about 0.014". The segment 21 merges into a distal tapered portion 23 that extends over a length of about 6 cm and may taper to about 0.002".

The guidewire includes an inner coil 26 disposed within the outer coil 14 and extending from the region of the distal tip 16 of the shaft 10 to the tip weld 20. The inner coil is formed from a highly radiopaque material and may be formed from the same material, such as a platinum tungsten alloy, as the outer coil 14. The inner coil 26 is formed from a larger diameter wire than the wire from which the outer coil 14 is made. By way of example, the inner coil may be formed from a wire of the order of 0.002" to 0.003" diameter. The inner coil 26 is attached to the region of the distal tip 16 of the shaft 10 at a braze joint 28 and at its distal end to the tip weld 20.

From the foregoing, it will be appreciated that the portion of the coil arrangement that includes both the large diameter wire inner coil 26 and the small diameter wire coil 14 will be more radiopaque than the portion of the coil assembly that includes only the small diameter wire outer coil 14 which will appear less dark on the fluoroscope. Thus, when viewed on a fluoroscope, the guidewire will exhibit a heavy dark distal portion and a moderately shadowed proximal portion.

Thus, I have described a guidewire incorporating a dual concentric coil configuration having varied degrees of radiopacity at its distal region. It should be understood, however, that the foregoing description of the invention is intended merely to be illustrative thereof and that other embodiments and modifications may be apparent to those skilled in the art without departing from its spirit.

Having thus described the invention what I desire to claim and secure by letters patent is:

1. A guidewire for use with a catheter comprising:
    an elongate flexible shaft;
    an outer helical coil mounted to and about the distal portion of the shaft, the distal tip of the outer coil extending distally beyond the distal tip of the shaft;
    a smoothly rounded outer tip member attached to the distal end of the outer coil;
    an inner helical coil contained within the distal end of the outer coil, the inner coil being attached at its proximal end to the distal end of the shaft and, at its distal end to the tip member;
    both of said coils being formed from a highly radiopaque material;
    the outer coil being formed from wire that is of lesser thickness, measured in a radial direction from the center of the coil than that of the wire from which the inner coil is formed.

2. A guidewire as defined in claim 1 wherein the portion of the shaft that is received within the coils is tapered.

3. A guidewire as defined in claim 2 wherein the taper is a step taper.

4. A guidewire as defined in any of claims 1-3 further comprising:
    the radial thickness of the wire from which the outer coil is formed being no greater than one-half of the radial thickness of the wire from which the inner coil is formed.

5. A guidewire as defined in any of claims 1-3 wherein the radial thickness of the wire from which the outer coil is formed is about 0.001" and wherein the radial thickness of the wire from which the inner coil is formed is at least 0.002".

6. A guidewire as defined in claim 4 wherein the length of the guidewire is about 175 cm.

7. A guidewire as defined in claim 5 wherein the length of the guidewire is about 175 cm.

8. A guidewire as defined in any of claims 1-3 wherein the portion of the guidewire defined by the inner helical coil is substantially more radiopaque than the portion of the guidewire defined by that portion of the outer helical coil that is disposed proximally of the inner helical coil.

9. A guidewire as defined in claim 4 wherein the portion of the guidewire defined by the inner helical coil is substantially more radiopaque than the portion of the guidewire defined by that portion of the outer helical coil that is disposed proximally of the inner helical coil.

10. A guidewire as defined in claim 5 wherein the portion of the guidewire defined by the inner helical coil is substantially more radiopaque than the portion of the guidewire defined by that portion of the outer helical coil that is disposed proximally of the inner helical coil.

11. A guidewire defined in claim 6 wherein the portion of the guidewire defined by the inner helical coil is substantially more radiopaque than the portion of the guidewire defined by that portion of the outer helical coil that is disposed proximally of the inner helical coil.

12. A guidewire as defined in claim 4 wherein the cross-section of the wire of at least one of the inner and outer coils is circular and where said radial thickness comprises the diameter of the wire.

13. A guidewire as defined in claim 5 wherein the cross-section of the wire of at least one of the inner and outer coils is circular and where said radial thickness comprises the diameter of the wire.

14. A guidewire as defined in claim 8 wherein the cross-section of the wire of at least one of the inner and outer coils is circular and where said radial thickness comprises the diameter of the wire.

15. A guidewire as defined in claim 9 wherein the cross-section of the wire of at least one of the inner and outer coils is circular and where said radial thickness comprises the diameter of the wire.

16. A guidewire as defined in claim 10 wherein the cross-section of the wire of at least one of the inner and outer coils is circular and where said radial thickness comprises the diameter of the wire.

* * * * *